United States Patent [19]

Summers et al.

[11] Patent Number: 5,245,098

[45] Date of Patent: Sep. 14, 1993

[54] PROCESS FOR PREPARATION OF NON-CONJUGATED DIOLEFINS

[75] Inventors: Gabriel J. Summers; Fernando J. Hamilton, both of Akron, Ohio

[73] Assignee: The University of Akron, Akron, Ohio

[21] Appl. No.: 823,321

[22] Filed: Jan. 21, 1992

[51] Int. Cl.$^5$ ............................................. C07C 1/26
[52] U.S. Cl. ................................. 585/612; 585/601; 585/603; 585/632
[58] Field of Search ............... 585/601, 603, 612, 632

[56] References Cited

U.S. PATENT DOCUMENTS

| | | |
|---|---|---|
| 3,904,704 | 9/1975 | Bryson . |
| 3,933,769 | 1/1976 | Lal et al. . |
| 3,991,262 | 11/1976 | Lal et al. . |
| 4,228,313 | 10/1980 | Cardenas et al. ............ 585/612 |

OTHER PUBLICATIONS

Booth, G. et al., *J. Chem. Soc.*, pp. 3238–3241 (1965).
Dang, H. P. et al., *Tetrahedron Letters*, No. 2, 191–194 (1978).
Derguini-Boumechal, F. et al., *Tetrahedron Letters*, No. 13, 1181–1184 (1977).
Kende, A. S. et al., *Tetrahedron Letters*, No. 39, 3375–3378 (1975).
Tamao, K. et al. *Bull. Chem. Soc. Japan*, 49(7), 1958–1969 (1976) (Tamao et al. I).
Tamao, K. et al., *J. Organometallic Chem.*, 55, C91–C94 (1973) (Tamao et al. II).
Tamao, K. et al., *J. Am. Chem. Soc.*, 94 (26), 9268–9269 (1972) (Tamao et al. III).
Zembayashi, M. et al., *Tetrahedron Letters*, No. 21, 1719–1722 (1975).
Kiso, Y. et al. *J. Organometallic Chem.*, 50 C12–C14 (1973).
Lal, J. et al., "Polymers of 1,4-Hexadienes", J. E. Mark and J. Lal, eds., ACS Symposium Series No. 193, Paper No. 8, pp. 171–194 (1882) (Lal et al I).
Lal, J. et al., *J. Polymer Sci., Polymer Symposium* 74, 141–164 (1986) (Lal et al. II).

*Primary Examiner*—Patrick P. Garvin
*Assistant Examiner*—E. D. Irzinski
*Attorney, Agent, or Firm*—Oldham, Oldham & Wilson Co.

[57] ABSTRACT

The monomer 5-methyl-1,4-hexadiene (5-MHD), uncontaminated with 4-methyl-1,4-hexadiene (4-MHD), or other hydrocarbons, is obtained by reacting 1-chloro-2-methylpropene with allylmagnesium bromide in equimolar amounts under gentle reflux at atmospheric pressure in an organic solvent medium (diethyl ether) and in the presence of a catalytic amount of a dichloro-[1,2-bis(dimethylphosphino)ethane]nickel (II) in an inert atmosphere. The allyl magnesium bromide is added dropwise with stirring with a mixture of 1-chloro-2-methylpropene and catalyst in the solvent at room temperature. The solvent is separated from the product by distillation, giving substantially pure product. Absence of other hydrocarbons in either the crude product or the pure product may be shown by $^1$H NMR, $^{13}$C NMR and GC analysis. Other nonconjugated diolefins can be prepared in an analogous manner using an alkenyl halide and an alkenyl Grignard reagent which upon cross coupling will give the desired non-conjugated diene.

7 Claims, No Drawings

PROCESS FOR PREPARATION OF NON-CONJUGATED DIOLEFINS

TECHNICAL FIELD

This invention relates to a process which relates to a process for preparing non-conjugated diolefins and in particular 5-methyl-1,4-hexadiene (5-MHD).

BACKGROUND OF THE INVENTION

A sulfur vulcanizable copolymer obtained by copolymerization of 1-hexene with a small amount (typically 3-5 mol percent) of methylhexadiene, which may be either a mixture of 4-methyl-1,4-hexadiene (4-MHD) and 5-methyl-1,4-hexadiene (5-MHD), or 5-MHD in substantially pure form, yields on vulcanization a rubber having outstanding biocampatibility and very high flex resistance, excellent ozone resistance, good compression resistance and high damping. This rubber is made and sold by Goodyear Tire and Rubber Company, Akron, Ohio USA, under the trademark "HEXSYN®". Because of its outstanding biocampatibility and its flex resistance, this rubber has become the elastomer of choice in biomedical devices, including heart valves and diaphragms for artificial hearts and assist devices, e.g., a left ventricle assist devices (LVAD) and artificial finger joints. Synthesis of such rubbers and their use in biomedical applications is described in Lal et al *Journal of Polymer Science: Polymer Symposium* 74, 141-164 (1986). As this article points out, 5-MHD is more reactive than 4-MHD and has a reactivity essentially equal to that of 1-hexene. As a consequence, 5-MHD readily copolymerizes with 1-hexene while 4-MHD is poorly incorporated. This leads to copolymers of non-uniform composition.

Lal et al., "Elastomers and Rubber Elasticity", J. E. Mark and J. Lal, eds., ACS Symposium Series No. 193, pp 171-194, (1982) describe copolymerization of 1-hexene with substantially pure 5-MHD, which is obtained by fractionation of a mixture of 4-MHD and 5-MHD.

Other references describing polymerization of alpha-olefins including 1-hexene with non-conjugated dienes including 5-MHD and mixture of 4-MHD and 5-MHD include U.S. Pat. Nos. 3,933,769 and 3,991,262 to Lal et al (both 1976).

U.S. Pat. No. 3,904,704 to Bryson describes a process for production of non-conjugated diolefins by codimerization of ethylene or other alpha-olefin and a conjugated diolefin at high temperature and pressure in the presence of a catalyst. The process is described with particular reference to production of a mixture of 4-methyl-1,4-hexadiene (4-MHD) and 5-methyl-1,4-hexadiene (5-MHD) from ethylene and isoprene. Ratios of 4-MHD and 5-MHD in this product vary widely depending on conditions used, according to data in the patent. A mixture of 4-MHD and 5-MHD is the diene comonomer for synthesis of "Hexsyn" as disclosed in Lal et al *Journal of Polymer Science* (1986) cited supra. As Lal et al (1982) and (1986) disclose, it is necessary to fractionate the mixture of 4-MHD and 5-MHD if one desires either monomer in pure form. Fractionation is difficult and time-consuming because the boiling points of 4-MHD and 5-MHD are very close (88°-89° C. and 92.8° C. respectively, as reported by Lal et al). Both Lal et al articles also disclose that a diene monomer feed of pure 5-MHD is preferable to the mixture for the reasons stated earlier herein. Nevertheless, routes for preparing pure 5-MHD have not gained acceptance.

Synthesis of a wide variety of hydrocarbons by nickel phosphine complex-catalyzed Grignard coupling, i.e., by cross-coupling of a alkyl, aryl or alkenyl Grignard reagent with an aryl or alkenyl halide, is disclosed in Tamao et al, *Bulletin of the Chemical Society of Japan*, 49(7), 1958-1969 (1976). Numerous specific reactions are disclosed but none relate to the production of a non-conjugated diolefin and the only reaction for preparing a conjugated diolefin is for the preparation of 2,3-dimethyl-1,3-butadiene from 2-bromo-1-propene and isopropylmagnesium bromide. Yields reported by the authors vary widely, from less than 5% to 100%. Preparation of 2,3-dimethyl-1,3-butadiene from 2-bromo-1-propene and isopropylmagnesium bromide according to Tamao et al was carried out for 20 hours at reflux, with a 79% yield as determined by gas chromatography (GC).

Although Grignard coupling reactions have been known for years, no one has use such reactions commercially for preparation of a non-conjugated diene hydrocarbon as far as the inventors are aware. In fact, as far as the inventors are aware no one has prepared pure 5-MHD free of contamination with structural isomers, by any synthetic route. There remains a need for a process for producing 5-MHD without co-producing appreciable quantities of isomers, in order to provide essentially pure 5-MHD as a diene monomer for the production of polyolefin/diene rubbers.

SUMMARY OF THE INVENTION

This invention provides a process for the production of a non-conjugated diene by reacting an alkenyl halide of the formula (I)

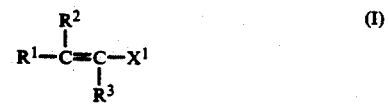

with an alkenyl Grignard reagent of the formula (II)

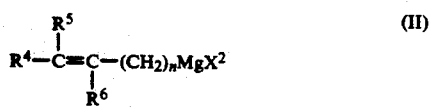

in the presence of an organometallic catalyst to produce a non-conjugated diene of the formula (III)

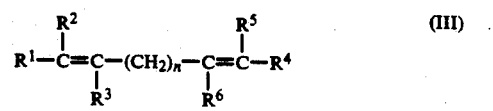

In the above formulas:

$R^1$ and $R^2$ may be the same or different and each is hydrogen, a lower alkyl radical or aryl;

$R^3$ is hydrogen, lower alkyl or aryl;

$R^4$ and $R^5$ may be the same or different and each is hydrogen, lower alkyl or aryl;

$R^6$ is hydrogen, lower alkyl or aryl;

$X^1$ and $X^2$ may be the same or different and each is chlorine, bromine or iodine; and n is a positive integer from 1 to about 12.

In a preferred embodiment of this invention, 1-chloro-2-methylpropene (I-a) and allylmagnesium bromide (II-a) are reacted in essentially equimolar proportions to give 5-methyl-1,4-hexadiene (5-MHD) (III-a) in the substantial absence of any isomers thereof. This reaction may be shown by the following equation:

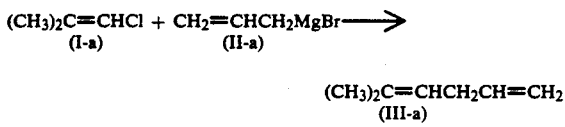

$$(CH_3)_2C{=}CHCl + CH_2{=}CHCH_2MgBr \longrightarrow$$
$$(I\text{-}a) \qquad (II\text{-}a)$$

$$(CH_3)_2C{=}CHCH_2CH{=}CH_2$$
$$(III\text{-}a)$$

The above reactions may be carried out in a suitable organic solvent, e.g., diethyl ether, and in the presence of a catalytic amount of nickel phosphine catalyst at atmospheric pressure.

DETAILED DESCRIPTION

This invention will be described in further detail with particular reference to the preferred embodiment thereof, in which 1-chloro-2-methylpropene (I-a) and allylmagnesium bromide (II-a) are reacted in essentially equimolar amounts in the presence of nickel phosphine halide catalyst and a suitable organic solvent.

A nickel phosphine halide catalyst is a dihalodiphosphinenickel (II) complex, which may be prepared as described in Tamao et al cited supra or as described in Booth et al, *Journal of the Chemical Society* (London), pages 3238–3241 (1965). Such complex consists essentially of a nickel (II) halide (typically the chloride) and one mol of a bidentate ligand which is characterized by tertiary phosphorus atoms connected by an alkylene group of 1–4 carbon atoms with 2 hydrocarbon (e.g., methyl, ethyl or phenyl) groups bonded to each of the phosphorus atoms. A preferred complex of this type for the purpose of this invention is dichloro-[1,2-bis(dimethylphosphino)ethane]nickel(II), which may be abbreviated Ni(dmpe)Cl$_2$.

The preferred solvent for carrying out the reaction according to this invention is diethyl ether (i.e., "ether"). Other suitable solvents include other lower alkyl ethers (e.g., dimethyl ether) and tetrahydrofuran (THF). Ether is preferable to tetrahydrofuran (THF) because ether has a lower boiling point than THF; also, the Grignard reagent is commonly obtained commercially in an ether solution.

It is preferred to charge equimolar amounts of the alkenyl halide and the Grignard reagent to a reactor in the practice of this invention. It is important to add the Grignard reagent to a mixture of the alkenyl halide and a catalytic amount of the dihalodiphosphinenickel (II) complex. The catalyst is essential since no reaction takes place without it.

The reaction of this invention can be carried out under mild reaction conditions, i.e., atmospheric pressure and gentle reflux. The reaction is exothermic so that no external heat is necessary. The reaction should be carried out in an inert atmosphere, e.g., argon or nitrogen.

The reaction of the present invention is stereospecific, i.e., there is essentially no co-production of any isomer of 5-MHD (as for example 4-MHD). Also, cross coupling between the alkenyl halide and the Grignard reagent takes place to the virtual exclusion of any auto-reaction of either the alkenyl halide or the Grignard reagent with itself. As a result, the desired 5-MHD is obtained in the substantial absence of any other hydrocarbons (including 4-MHD), and both reagents are essentially completely consumed when equimolar quantities are used so that the principal impurity is the solvent, diethyl ether. Conversion is essentially 100%, i.e., substantially all of the Grignard reagent and substantially all of the alkenyl halide reagent are consumed when equimolar quantities are used.

The reaction product can be purified by simple distillation using a packed column. Some loss of product 5-MHD occurs because of the high volatility of the product and the fact that it forms an azeotrope with diethyl ether. This loss may be significant when distillation procedures are not optimized. Good separation can be achieved if a packed column of sufficient height (and therefore containing a sufficient number of theoretical plates) is used. Yields of essentially pure 5-MHD may vary from about 50% to about 80% of theoretical, depending largely on recovery conditions. The pure product has a purity greater than 95% and is substantially without contamination by structural isomers.

More broadly, other nonconjugated dienes can be prepared by appropriate choice of the alkenyl halide (or haloalkene) (I) and the Grignard reagent (II).

The halogen of the alkenyl halide (I) may be either chlorine, bromine or iodine, chlorine or bromine usually being preferred. The groups $R^1$ and $R^2$ may be the same or different but are preferably the same. Each may be hydrogen, a lower alkyl radical containing from 1 to about 6 carbon atoms, e.g., methyl, ethyl, propyl or butyl; or aryl such as phenyl or tolyl, with methyl, ethyl or phenyl and especially methyl being preferred. When $R^1$ or $R^2$ (or both) is aryl, the aryl radical may be either substituted or unsubstituted but is preferably either monocyclic (i.e., containing one aromatic ring) or bicyclic (i.e., containing 2 aromatic rings), more preferably monocyclic. When $R^1$ and $R^2$ are the same, the product will be essentially pure except for solvent (essentially no other hydrocarbons will be coproduced). When $R^1$ and $R^2$ are different, there are cis and trans isomers with the possibility that the two will be coproduced. Therefore it is preferred that $R^1$ and $R^2$ be the same.

The alkenyl halide is a vinylic compound, i.e., one in which the halogen is attached directly to a carbon atom of the alkene functionality. Preferably this carbon atom also has an unsubstituted hydrogen atom attached to it. In other words, $R^3$ is preferably hydrogen. More broadly, $R^3$ can be hydrogen, lower alkyl (1 to about 6 carbon atoms) or aryl (preferably monocyclic or bicyclic, more preferably monocyclic such as phenyl or p-tolyl).

Representative alkenyl halide reactants (I) according to this invention include vinyl chloride, 1-chloro-2-methyl-1-propene (previously mentioned), 1-chloro-3-methyl-1-butene, 1-chloro-1-methyl-1-pentene and 2-chloro-1,1-diphenylethylene and their bromo analogs in addition to 2-chloro-1-propene and 2-bromo-1-propene (previously mentioned).

Suitable Grignard reagents (II) include 3-butenylmagnesium bromide and 3-butenylmagnesium chloride in addition to the previously mentioned allylmagnesium bromide and its chloro analog allylmagnesium chloride. In general, vinylic Grignard reagents, e.g., vinylmagnesium bromide, have lower reactivities than allylic Grignard reagents (e.g., allylmagnesium bromide) and Grignard reagents in which the —MgBr (or —MgCl) group is more remote from the double bond than is the case in allylic Grignard reagents. Therefore n in formulas (II) and (III) is a positive integer, 1 or higher, and is not 0. For reasons of practicality, the maximum value of n is not over about 12, preferably not over about 6, more preferably not over about 4. Most preferably n=1. The Grignard reagent is preferably alpha olefinic in character, that is, it preferably has an unsubstituted $CH_2$=group. In other words, it is preferred that both carbon atoms which are joined by the double bond be unsubstituted. Therefore $R^4$ and $R^5$ in formulas (II) and (III) are preferably hydrogen, although they can be the same or different and each may be hydrogen, lower alkyl (1 to about 6 carbon atoms) or aryl (preferably monocyclic or bicyclic aryl, more preferably monocyclic aryl such as phenyl or p-tolyl). Similarly, $R^6$ is preferably hydrogen but can be hydrogen, lower alkyl (1 to about 6 carbon atoms) or aryl (preferably monocyclic or bicyclic aryl, more preferably monocyclic aryl such as phenyl or p-tolyl).

Representative nonconjugated dienes (III) which can be prepared in accordance with this invention include 1,4-hexadiene, 1,5-hexadiene, 6-methyl-1,5-heptadiene, 5,5-diphenyl-1,4-pentadiene and 5-methyl-1,4-octadiene in addition to 5-MHD. The compound 5-methyl-1,4-octadiene, like 5-MHD, is a suitable diene monomer for synthesis of specialty rubbers.

The catalysts, solvent and reaction conditions disclosed previously for the preparation of 5-MHD from 1-chloro-2-methylpropene (I-a) and allylmagnesium bromide (II-a) are applicable generally to the preparation of nonconjugated dienes (III) by reaction of any desired alkenyl halide (I) and alkenyl Grignard reagent (II). As in the reaction of (I-a) with (II-a), products are produced in substantially pure form in accordance with this invention, with the solvent being the principal impurity in most cases. In any case, the reaction taking place is a clean cross-coupling without self-reaction of either the alkenyl halide or the Grignard reagent, and without production of isomers of the desired product.

Products of this invention are useful as diene monomers for copolymerization with an alpha olefin or mixture thereof in order to produce elastomeric polyolefins.

EXAMPLES

This invention will now be described further with reference to specific embodiments thereof, as illustrated in the following examples.

The abbreviation, "FW", in the examples denotes formula weight (g/mol).

Catalyst Preparation

Synthesis of dichloro-[1,2-bis(dimethylphosphino)ethane]nickel (II) [Ni(dmpe)Cl$_1$]: FW 279.738

Under an argon atmosphere, a solution of hydrated nickel chloride (2.47 g) in absolute ethanol (25 mL) was added dropwise with stirring to 1,2-bis(dimethylphosphino)ethane (3.00 g) in ethanol (50 mL). The resulting orange solution was concentrated in vacuo. The product was precipitated by successive addition of acetone (30 mL) and benzene (86 mL) to give a 2:1 complex of impure, unstable dichloro-[1,2-bis(dimethylphosphino)ethane]nickel(II) as orange crystals. A mixture of the impure 2:1 complex (3.0 g) and hydrated nickel chloride (3.5 g) in ethanol (100 mL) was heated to reflux for 1 hr. The resulting brown-bronze precipitate was filtered, washed with cold ethanol and vacuum dried to give 2.712 g (49%) of Ni(dmpe)Cl$_2$ as bronze crystals.

EXAMPLE 1

Synthesis of 5-methyl-1,4-hexadiene [5-MHD]: FW 96.173

Under an argon atmosphere and apparatus setup for reflux equipped with a cold finger packed with dry ice, allylmagnesium bromide (0.0552 mol, 55.22 mL of 1.0 M solution in diethyl ether) was added dropwise with stirring to a mixture of 1-chloro-2-methylpropene (5.0 g, 0.0552 mol), and a catalytic amount of Ni(dmpe)Cl$_2$ (0.0890 g), at room temperature. An exothermic reaction occurred as evidenced by a gentle reflux with the subsequent formation of a white precipitate. The resulting yellow solution was allowed to cool and stirred at room temperature (25° C.) for 1 hour. The reaction mixture was then heated to reflux for 2 hr. The reaction was monitored by gas chromatography which indicated the formation of significant amounts of 5-MHD and the complete disappearance of 1-chloro-2-methylpropene after 2 hr. The mixture was allowed to stir at room temperature overnight. (Stirring overnight can be omitted since it had no effect on the reaction). After aqueous quenching, the ethereal layer was dried with sodium sulfate and the weight recorded with careful handling of the volatile ethereal mixture. Gas chromatographic (GC) analysis of the crude product gave 4.6797 g (88%) of 5-methyl-1,4-hexadiene, with no isomers or unreacted reagents detected. The results obtained are consistant with GC traces for mixtures of known compositions of pure samples of diethyl ether and 5-MHD. Furthermore, $^1$H NMR spectroscopic analysis of the crude product confirmed the formation of 5-MHD with diethyl ether as the major contaminant.

The crude sample was concentrated by removal of diethyl ether by simple distillation through a Vigreux column. Final distillation of the product through a Vigreux column yielded 2.693 g (51%) of pure (ether-free) 5-MHD: bp: 91°–92° C. GC: one peak $t_r$=2.822, 99.4% purity. $^1$H NMR (CDCl$_3$): δ1.602 (s, 3H), 1.700 (s, 3H), 2.722 (t, 2H), 4.901–5.030 (m, 2H), 5.110–5.163 (m, 1H), 5.713–5.825 ppm (m, 1H). $^{13}$C NMR (CDCl$_3$): δ17.572, 25.655, 32.414, 114.050, 121.569, 132.731, 137.473 ppm.

The following observations were made:

1. No reaction occurred in the absence of catalyst at reflux for six hours as evidenced by GC analysis.

2. The apparatus was equipped with a cold finger in order to reduce the loss of volatile 5-MHD and diethyl ether during reflux and upon quenching the reaction. In an apparatus of larger than laboratory scale, a condenser should be used so that substantially all 5-MHD in the gaseous phase in the reaction vessel is condensed and returned to the reaction medium, and does not vent into the atmosphere.

3. Significant loss of 5-MHD occurred upon final distillation due to volatility and azeotropic distillation with ether.

4. The procedure for purifying the crude 5-MHD product in this example was not optimized. It is believed that the Vigreux column used for purification of the crude product did not contain enough theoretical plates for recover of pure 5-MHD in high yield.

EXAMPLE 2

Synthesis of 5-methyl-1,4-hexadiene [5-MHD]

The procedure of example 1 was followed except that (1) quantities were as given below, and (2) the reaction mixture was not heated to reflux after complete addition of the Grignard reagent. Such heating was not necessary since the reaction was complete without heating as evidenced by GC analysis. The crude sample was concentrated and purified by simple distillation using a column packed with glass beads. Quantities in this example were as follows: allylmagnesium bromide, 0.5522 mol (552.2 mL of 1.0 M solution in diethyl ether); 1-chloro-2-methylpropene, 50.0 g, 0.5522 mol; Ni(d-mpe)Cl$_2$, 0.3100 g. Yield of crude product 5-methyl-1,4-hexadiene (5-MHD) (by gas chromatographic analysis), 41.12 g (77%). Yield of pure 5-MHD: 35 g (66%); purity, (GC) 97%. As in Example 1, gas chromatographic analysis showed no isomers or unreacted reagents. The higher yield of pure 5-MHD in this example, as compared to example 1, is believed to be due to the fact that the packed column used for purification in this example afforded more theoretical plates with consequent better separation of product 5-MHD from ether.

EXAMPLE 3

Synthesis of 5-methyl-1,4-octadiene

The procedure of Example 1 is followed, using equimolecular quantities of 1-chloro-2-methyl-1-pentene (I-b) as the alkenyl halide and allylmagnesium bromide (II-a) as the Grignard reagent. The compound 5-methyl-1,4-octadiene (III-b) is obtained.

EXAMPLE 4

Synthesis of Various non-conjugated dienes

The procedure of example 1 is followed, using equimolar quantities of an alkenyl halide (I) and a Grignard reagent (II) as indicated in Table I below. A non-conjugated diene (III), also is indicated in Table I below, is obtained.

TABLE I

| | Representative Reactants and Products | | |
|---|---|---|---|
| | Alkenyl halide I | Grignard Reagent II | Non-conjugated diene III |
| c | CH$_2$=CHCl | CH$_2$=CHCH$_2$MgBr | CH$_2$=CHCH$_2$CH=CH$_2$ |
| d | (CH$_3$)$_2$C=CHCl | CH$_2$=CHCH$_2$CH$_2$MgBr | (CH$_3$)$_2$C=CHCH$_2$CH$_2$CH=CH$_2$ |
| e | (C$_6$H$_5$)$_2$C=CHCl | CH$_2$=CHCH$_2$MgBr | (C$_6$H$_5$)$_2$C=CHCH$_2$CH=CH$_2$ |

EXAMPLE 5

Polyolefin Synthesis

High purity 5-MHD (97% purity), prepared as described in Example 2, was utilized as a comonomer in the synthesis of a polyolefin rubber, following the procedure described below. The materials used for polymerization were as listed in Table 2.

TABLE II

| Material | Quantity |
|---|---|
| 1-Hexene | 15.1 mol (1272 g, 1890 mL) |
| 5-MHD | 0.390 mol (30.63 g, 42.21 mL) |
| Hexanes (solvent) | 7776 mL |
| Triethyl aluminum | 0.06482 mol (44.85 g, 64.82 mL) |
| Titanium trichloride | 0.03241 mol (5.0 g) in hexanes (20 mL) |

The quantities of 1-hexene and 5-MHD shown in Table II represent 98 mols of 1-hexene and 2 mols of 5-MHD per 100 mols of monomer.

The word, "hexanes", in Table II denotes that the hexane solvent was a mixture of isomeric hexanes. Normal hexane was the predominant isomer.

The apparatus comprised a 12 liter 3 necked round bottom flask equipped with a stirrer driven by an air motor, an oil bubbler, and a drying column. The drying column, consisting of a 5 liter round bottom flask fused to a 1 inch×27 inch (2.54 cm×68.58 cm) column with a ground glass stop cock and a 24/40 ground male joint, was fitted to the 12 liter flask. The 12 liter flask served as the polymerization flask and the 5 liter flask was a reservoir for the drying column.

All apparatus was heated overnight in an oven at 120° C., assembled hot and cooled under a flow of dry argon. Then the drying column was charged with activated neutral alumina and then fitted to the 12 liter flask. The polymerization flask was cooled to about 10° C. with a water bath while under a flow of argon.

Hexane (2000 mL) was charged to the drying column reservoir to prewet the column. After prewetting the column, 1-hexene and 5-MHD (quantities as shown in Table II) were added to the reservoir and passed through the column into the polymerization flask. The remainder of the hexane solvent (5776 mL) was then passed through the column under low positive argon pressure. After all monomers and solvent were passed through the column, the column was replaced with a water cooled reflux condenser and connected to the oil bubbler via Tygon tubing. At this point, the premix solution in the 12 liter flask was sparged with dry argon for 30 minutes.

The polymerization flask was then charged with tiethyl aluminum followed by delta-titanium trichloride (quantities as shown in Table II) in a dry hexane slurry.

Polymerization was carried out at 10° C. for 48 hours. The polymer was isolated by coagulation in methanol, cutting into small strips and drying to constant weight in a vacuum oven at 50° C.

1-Hexene and 5-MHD were observed to be essentially equally reactive. Consequently all quantities of both monomers entered into polymerization, and the quantity of the 5-MHD in the copolymer (2 mol percent) was essentially the same as in the monomer feed.

While this invention has been described with reference to preferred embodiments thereof, it is understood that these are by way of illustration and not limitation.

What is claimed is:

1. A process for preparing 5-methyl-1,4-hexadiene substantially free from any isomers thereof, which comprises reacting substantially equimolar quantities of a 1-halo-2-methylpropene and an allylmagnesium halide, wherein the halogens of said 1-halo-2-methylpropene and said allylmagnesium halide are chlorine or bromine, in the presence of a catalytic amount of a nickel phosphine catalyst, and recovering said 5-methyl-1,4-hexadiene substantially free from any isomers thereof.

2. A process according to claim 1 wherein said process is carried out in a solvent medium.

3. A process according to claim 1 wherein said catalyst is a dihalodiphosphinenickel (II) complex.

4. A process according to claim 1 wherein said process is carried out in the presence of a catalytic amount of dichloro-[1,2-bis(dimethylphosphino)ethane]nickel (II).

5. A process according to claim 4 wherein said process is carried out at atmospheric pressure in diethyl ether at reflux.

6. A process according to claim 1 wherein said 1-halo-2-methylpropene is 1-chloro-2-methylpropene.

7. A process according to claim 1 wherein said allylmagnesium halide is allylmagnesium bromide.

* * * * *